(12) United States Patent
Goto et al.

(10) Patent No.: US 9,011,804 B2
(45) Date of Patent: Apr. 21, 2015

(54) COBALT EXTRACTION METHOD
(71) Applicants: Kyushu University, National University Corporation, Fukuoka-shi, Fukuoka (JP); Sumitomo Metal Mining Co., Ltd., Tokyo (JP)
(72) Inventors: Masahiro Goto, Fukuoka (JP); Fukiko Kubota, Fukuoka (JP); Yuzo Baba, Fukuoka (JP)
(73) Assignees: Sumitomo Metal Mining Co., Ltd., Tokyo (JP); Kyushu University, National University Corp., Fukuoka (JP)
( * ) Notice: Subject to any disclaimer, the term of this patent is extended or adjusted under 35 U.S.C. 154(b) by 0 days.
(21) Appl. No.: 14/001,848
(22) PCT Filed: Nov. 2, 2012
(86) PCT No.: PCT/JP2012/078446
§ 371 (c)(1),
(2) Date: Aug. 27, 2013
(87) PCT Pub. No.: WO2013/069563
PCT Pub. Date: May 16, 2013
(65) Prior Publication Data
US 2014/0328737 A1 Nov. 6, 2014
(30) Foreign Application Priority Data

Nov. 9, 2011 (JP) .................................. 2011-245981
Mar. 13, 2012 (JP) .................................. 2012-056143
Aug. 10, 2012 (JP) .................................. 2012-178293
Oct. 10, 2012 (JP) .................................. 2012-225454

(51) Int. Cl.
*B01D 11/00* (2006.01)
*C22B 3/00* (2006.01)
(Continued)
(52) U.S. Cl.
CPC ......... *C22B 23/0461* (2013.01); *C01F 17/0006* (2013.01); *B01D 11/00* (2013.01);
(Continued)

(58) Field of Classification Search
None
See application file for complete search history.

(56) References Cited

FOREIGN PATENT DOCUMENTS

CN 101519427 A 9/2009
EP 0834581 A1 4/1998
(Continued)

OTHER PUBLICATIONS

Extended European Search Report for EP Application No. 12848105.8, mailed Jan. 22, 2014.
(Continued)

*Primary Examiner* — Melissa Swain
(74) *Attorney, Agent, or Firm* — Locke Lord LLP; Jeffrey D. Hsi

(57) ABSTRACT

The objective of the present invention is to selectively extract cobalt from an acidic solution containing a high concentration of manganese. This cobalt extraction method extracts cobalt from an acidic solution containing manganese and cobalt by subjecting the acidic solution to solvent extraction by means of a valuable metal extraction agent comprising an amide derivative represented by general formula (I). The valuable metal extraction agent is represented by the general formula. In the formula: $R^1$ and $R^2$ each represent the same or different alkyl group; $R^3$ represents a hydrogen atom or an alkyl group; and $R^4$ represents a hydrogen atom or any given group aside from an amino group bonded to the α carbon as an amino acid. Preferably, the general formula has a glycine unit, a histidine unit, a lysine unit, an aspartic acid unit, or an N-methylglycine unit. Preferably, the pH of the acidic solution is 3.5-5.5 inclusive.

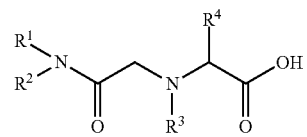

4 Claims, 4 Drawing Sheets

EXTRACTION OF COBALT WHEN USING A GLYCINAMIDE DERIVATIVE (EXAMPLE 1) AS AN EXTRACTION AGENT

(51) Int. Cl.
| | |
|---|---|
| *C01F 17/00* | (2006.01) |
| *C22B 3/26* | (2006.01) |
| *C22B 59/00* | (2006.01) |
| *C22B 23/00* | (2006.01) |
| *C07D 233/26* | (2006.01) |
| *C07C 237/06* | (2006.01) |
| *H01M 8/00* | (2006.01) |
| *H01M 10/54* | (2006.01) |

(52) U.S. Cl.
CPC ............ *C22B 3/0005* (2013.01); *C22B 3/0032* (2013.01); *C22B 59/00* (2013.01); *C22B 23/00* (2013.01); *C22B 23/0453* (2013.01); *C07D 233/26* (2013.01); *C07C 237/06* (2013.01); *H01M 8/008* (2013.01); *H01M 10/54* (2013.01)

(56) References Cited

FOREIGN PATENT DOCUMENTS

| EP | 2679693 A1 | 1/2014 |
|---|---|---|
| EP | 26824861 A1 | 1/2014 |
| JP | 2000-234130 A | 8/2000 |
| JP | 2010-174366 A | 8/2010 |
| JP | 2013-216656 A | 10/2013 |

OTHER PUBLICATIONS

Naganawa H, et al.; "A New "Green"Extractant of the Diglycol Amic Acid Type for Lanthanides"; Solvent Extraction Research and Development, vol. 14, pp. 151-159; (Jan. 2007).

Singh, D.K., et al.; "Extraction of Rare Earths and Yttrium With High Molecular Weight Carboxylic Acids"; Hydrometallurgy, 81, (Jan. 2006); pp. 174-181.

Extended European Search Report for 12847107.5 dated Feb. 6, 2014.

Holger, Stephan et al.; "Liquid-Liquid Extraction of Metal Ions with Amido Podands", Solvent Extraction and Ion Exchange, Taylor & Francis Group LLC, US, vol. 9, No. 3, Jan. 1, 1991: pp. 459-469.

K Shimojo et al.; Extraction Behavior and Separation of Lanthanides with a Diglycol Amic Acid Derivative and a Nitrogen-donor Ligand; Anal. Sci., 23, 1427-1430; vol. 23; Dec. 2007.

Hirofumi Morizono et al.; Liquid-liquid extraction of transition metal ions with an alkylhistidine extractant; Separation and Purification Technology, vol. 80, No. 2, Elsevier B.V., Jul. 29, 2011, p. 390-395.

International Search Report of PCT/JP2012/078446, Nov. 2012.

Office Action dated Apr. 8, 2014 for Japanese Appln. No. 2014-022868.

CAS Registration No. 1153237-54-7, Apr. 2014.
CAS Registration No. 1153399-39-3, Apr. 2014.
CAS Registration No. 1178468-85-3, Apr. 2014.
CAS Registration No. 1179174-30-1, Apr. 2014.
CAS Registration No. 1182789-10-1, Apr. 2014.
CAS Registration No. 1183588-00-2, Apr. 2014.
CAS Registration No. 1291231-35-0, Apr. 2014.

Notice of Reasons for Rejection issued to JP Application No. 2013-084951, mailed Jan. 14, 2014.

Pajewski et al; "The Effect of Midpolar Regime Mimics on Anion Transport Mediated by Amphiphilic Heptapeptides"; New Journal of Chemistry, French National Centre for Scientific Research, Nov. 2007, vol. 31, No. 11, pp. 1960-1972.

CAS Registration 1156229-80-9, Jan. 2014.

13C-NMR SPECTRUM OF A SAMPLE

<MEASUREMENT CONDITIONS>
SAMPLE CONCENTRATION : APPROX. 30 wt%/CDCl$_3$ SOLUTION
NUMBER OF SCAN : 1024 TIMES
BASE PEAK : $^{13}$C IN CDCl$_3$ ($\delta$ =76.9ppm)

EXTRACTION OF COBALT WHEN USING A GLYCINAMIDE
DERIVATIVE (EXAMPLE 1) AS AN EXTRACTION AGENT

EXTRACTION OF COBALT WHEN USING AN
N-METHYLGLYCINE DERIVATIVE (EXAMPLE 2)
AS AN EXTRACTION AGENT

EXTRACTION OF COBALT WHEN USING A HISTIDINAMIDE DERIVATIVE (EXAMPLE 3) AS AN EXTRACTION AGENT

EXTRACTION OF COBALT WHEN USING A CARBOXYLIC ACID-BASED COBALT EXTRACTION AGENT (COMPARATIVE EXAMPLE 1) AS AN EXTRACTION AGENT

COBALT EXTRACTION METHOD

CROSS-REFERENCE TO RELATED APPLICATIONS

This application is the national phase under 35 U.S.C. §371 of PCT International Application No. PCT/JP2012/078446, filed Nov. 2, 2012, which claims the benefit of Japanese Patent Application No. 2012-225454, filed Oct. 10, 2012; Japanese Patent Application No. 2012-178293, filed Aug. 10, 2012; Japanese Patent Application No. 2012-056143, filed Mar. 13, 2012; and Japanese Patent Application No. 2011-245981, filed Nov. 9, 2011, the entire contents of the aforementioned applications are hereby incorporated herein by reference.

TECHNICAL FIELD

The present invention relates to a cobalt extraction method.

BACKGROUND ART

Cobalt and rare earth metals are known as valuable metals and used for various applications in industry. Cobalt is used for positive electrode materials for secondary batteries, and, furthermore, superalloys (high strength heat-resistant alloys) used for e.g. jet engines for aircraft, and the like. Rare earth metals are used for fluorescent materials, negative electrode materials for nickel-hydrogen batteries, additives for magnets installed in motors, abrasives for glass substrates used for liquid crystal display panels and hard disk drives, and the like.

In recent years, energy savings have been strongly promoted, and in the automobile industry, conventional gasoline-engined cars are being rapidly replaced by hybrid cars and electric cars equipped with secondary batteries using cobalt and rare earth metals. In lighting equipment, conventional fluorescent lamps are being rapidly replaced by efficient three band fluorescent lamps using rare earth metals such as lanthan, cerium, yttrium, terbium and europium. The above cobalt and rare earth metals are scarce resources, and most of them depend on imports.

Yttrium and europium have been used for fluorescent substances in cathode ray tube television sets in analog broadcasting; however, in recent years, large numbers of cathode ray tubes have been put out of use because of the transition to liquid crystal television sets. Products which have rapidly spread, such as secondary batteries and three band fluorescent lamps, can be also easily expected to cause a large amount of waste in the future as used products. Thus, cobalt and rare earth metals, scarce resources, are treated as waste without recycling of the used products, which is not preferred in terms of resource savings and resource security. Nowadays, the establishment of a method for effectively retrieving valuable metals such as cobalt and rare earth metals from such used products is strongly demanded. Retrieval of cobalt from secondary batteries The above secondary batteries, incidentally, include nickel-hydrogen batteries, lithium ion batteries and the like, and in addition to cobalt, a rare earth metal, manganese is used for positive electrode materials thereof. In positive electrode materials in lithium ion batteries, the ratio of low cost manganese tends to be increased in place of high cost cobalt. The retrieval of valuable metals from used batteries has been attempted recently, and as one of the retrieval methods, there is a dry method in which used batteries are thrown into a furnace and melted, and metals and slag are separated to retrieve the metals. In this method, however, manganese moves to slag, and thus the metal that can be retrieved is only cobalt.

Further, a wet method is known, in which used batteries are dissolved in an acid and metals are retrieved using a separation method such as a precipitation method, a solvent extraction method or an electrowinning method. In the precipitation method, for example, a method in which the pH of a solution comprising cobalt and manganese is adjusted and a sulphurizing agent is added thereto to obtain a cobalt sulphide precipitate, and a method in which an oxidizing agent is added thereto to obtain a manganese oxide precipitate are known (see Patent Document 1). The methods, however, have problems such as the occurrence of coprecipitation, and it is difficult to completely separate cobalt and manganese.

It is known that when cobalt is retrieved as a metal by the electrowinning method, in a system in which a high concentration of manganese exists, manganese oxides are precipitated on the surface of an anode and deterioration of the anode is promoted. In addition, a peculiar colored fine manganese oxide is suspended in an electrolytic solution, and thus, for example, clogging of the filter cloth used for electrowinning and contamination of cobalt metal by the manganese oxide occur. Therefore, stable operations are difficult.

When cobalt is retrieved using the solvent extraction method, an acid extraction agent is widely used. As described above, however, nowadays manganese is used in large amounts for positive electrode materials in lithium ion batteries, and thus a high concentration of manganese exists in the solution in the batteries. Efficient extraction agents which selectively and efficiently extract cobalt from such a system do not exist in the existing circumstances.

In addition to recycling used batteries, in cobalt smelting which is currently carried out to produce cobalt, a raw material is a nickel ore such as a nickel oxide ore. The percentage of manganese is however higher than that of cobalt in the nickel oxide ore, and the existing percentage thereof is about 5 to 10 times that of cobalt. When cobalt is smelted, separation from manganese is a major problem.

Patent Document 1: Japanese Unexamined Patent Application, Publication No. 2000-234130

Non-Patent Document 1: K. Shimojo, H. Naganawa, J. Nora, F. Kubota and M. Coto; Extraction behavior and separation of lanthanides with a diglycol amic acid derivative and a nitrogen-donor ligand; Anal. Sci., 23, 1427-30, 2007 December.

DISCLOSURE OF THE INVENTION

Problems to be Solved by the Invention

An object of the present invention is to provide a method for selectively extracting cobalt from an acid solution comprising a high concentration of manganese.

As a result of repeated intensive investigation to solve the above problem, the present inventors found that the above object could be achieved by using a valuable metal extraction agent comprising an amide derivative represented by the following general formula (I), completing the present invention.

Means for Solving the Problems

Specifically, the present invention provides as follows.

(1) The present invention is a cobalt extraction method, wherein an acid solution containing manganese and cobalt is subjected to solvent extraction by a valuable metal extraction agent comprising an amide derivative represented by the following general formula (I) to extract the cobalt from the acid solution:

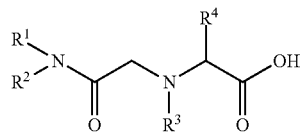

(wherein, $R^1$ and $R^2$ each represent the same or different alkyl groups; the alkyl group can be a straight chain or a branched chain; $R^3$ represents a hydrogen atom or an alkyl group; and $R^4$ represents a hydrogen atom or any group other than an amino group, which is bound to the α carbon as an amino acid).

(2) The present invention is also the cobalt extraction method according to (1), wherein the amide derivative is any one or more of glycinamide derivatives, histidinamide derivatives, lysinamide derivatives, aspartic acid amide derivatives and N-methylglycine derivatives.

(3) The present invention is also the cobalt extraction method according to (1) or (2), wherein the acid solution is subjected to the solvent extraction with the pH of the acid solution adjusted to a range of 3.5 or more to 5.5 or less.

Effects of the Invention

According to the present invention, cobalt can be selectively extracted from an acid solution comprising a high concentration of manganese.

PREFERRED MODE FOR CARRYING OUT THE INVENTION

Figure 1:
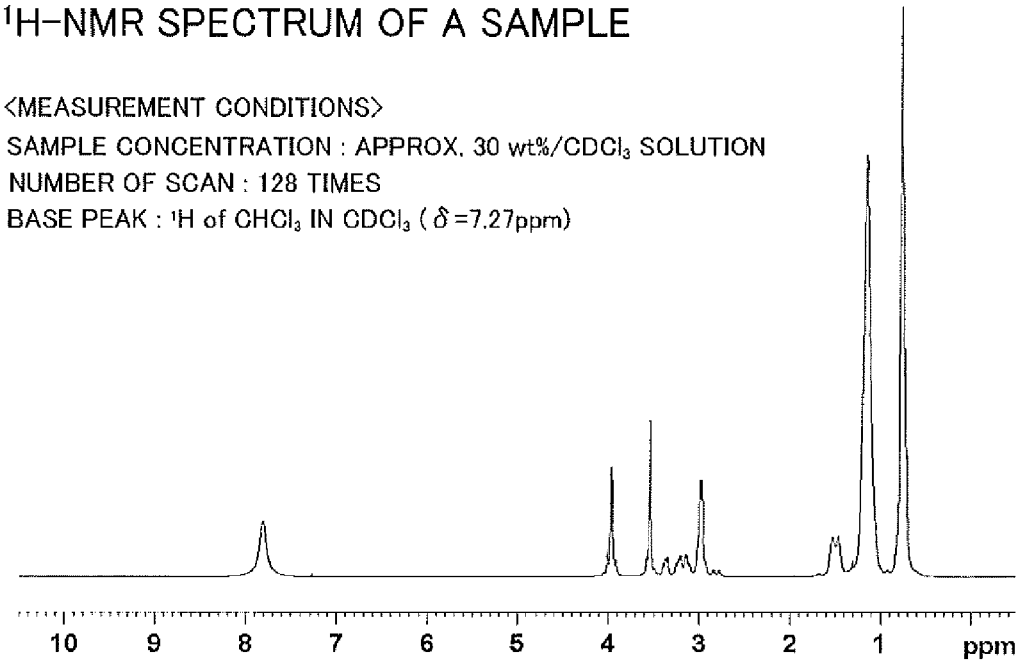
FIG. 1 is a figure showing a $^1$H-NMR spectrum of a glycinamide derivative synthesized in Example 1.

The specific embodiments of the present invention will now be described in detail. It should be noted, however, that the present invention is not restricted to the following embodiments and can be carried out with proper modification within the scope of the object of the present invention. Cobalt extraction method In the cobalt extraction method of the present invention, cobalt is extracted from an acid solution by solvent extraction by a valuable metal extraction agent comprising an amide derivative represented by the following general formula (I).

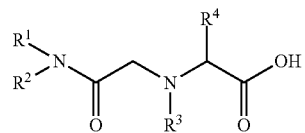

In the formula, substituents $R^1$ and $R^2$ each represent the same or different alkyl groups. The alkyl group can be a straight chain or a branched chain. $R^3$ represents a hydrogen atom or an alkyl group. $R^4$ represents a hydrogen atom or any group other than an amino group, which is bound to the α carbon as an amino acid. In the present invention, lipophilicity is increased by introducing alkyl groups into the amide skeleton, and the compound can be used as an extraction agent.

The above amide derivative is any one or more of glycinamide derivatives, histidinamide derivatives, lysinamide derivatives, aspartic acid amide derivatives and N-methylglycine derivatives. When the amide derivative is a glycinamide derivative, the above glycinamide derivative can be synthesized by the following method. First, a 2-halogenated acetyl halide is added to an alkylamine having a structure represented by $NHR^1R^2$ ($R^1$ and $R^2$ are the same as the above substituents $R^1$ and $R^2$), and the hydrogen atom of amine is substituted with a 2-halogenated acetyl by the nucleophilic substitution reaction to obtain a 2-halogenated (N,N-di)alkylacetamide.

Next, the above 2-halogenated (N,N-di)alkylacetamide is added to glycine or an N-alkylglycine derivative, and one of the hydrogen atoms of the glycine or N-alkylglycine derivative is substituted with an (N,N-di)alkylacetamide group by the nucleophilic substitution reaction. A glycine alkylamide derivative can be synthesized by the two-step reactions.

A histidinamide derivative, a lysinamide derivative or an aspartic acid amide derivative can be synthesized by substituting glycine with histidine, lysine or aspartic acid. The extraction behavior of lysine and aspartic acid derivatives is, however, thought to be within the range of the results obtained by using a glycine derivative and a histidinamide derivative according to the complex stability constant of manganese, cobalt and the like, which are targets.

To extract valuable metal ions using an extraction agent synthesized by the above method, with an acid aqueous solution comprising the objective valuable metal ions being adjusted, the acid aqueous solution is added to an organic solution of the above extraction agent, and mixed. Therefore, the objective valuable metal ions can be selectively extracted in the organic phase.

The organic solvent after extraction of the valuable metal ions is collected, and to this, a starting solution for back extraction is added and stirred to separate the objective valuable metal ions by extraction to an organic solvent, which starting solution is adjusted to a pH lower than that of the above acid aqueous solution. The objective valuable metal ions can be further retrieved from the organic solvent in an aqueous solution by back extraction of the objective valuable metal ions. As a solution for back extraction, for example, an aqueous solution in which nitric acid, hydrochloric acid or sulfuric acid is diluted is suitably used. In addition, the objective valuable metal ions can be concentrated by suitably changing the ratio of the organic phase and the aqueous phase.

Any organic solvent can be used, as long as an extraction agent and the extracted species of metals are dissolved with the solvent, and examples thereof include chlorine-based solvents such as chloroform and dichloromethane, aromatic hydrocarbons such as benzene, toluene and xylene, aliphatic hydrocarbons such as hexane, and the like. These organic solvents can be used individually, or two or more organic solvents can be mixed, and alcohols such as 1-octanol can be mixed therewith.

The concentration of the extraction agent can be properly set depending on the types and concentrations of valuable metals. In addition, the equilibrium arrival time varies depending on the types and concentrations of valuable metals and the amounts of extraction agent to be added, and thus the stirring time and extraction temperature can be suitably set depending on the conditions of an acid aqueous solution of valuable metal ions and an organic solution of the extraction agent. The pH of an acid aqueous solution comprising metal ions can be also suitably adjusted depending on the types of valuable metal.

Extraction of Cobalt

When cobalt is efficiently retrieved from an acid aqueous solution containing cobalt and manganese, any amino derivative of the above amino derivatives can be used as an extraction agent. Among these, it is preferred to use an N-methylglycine derivative or a histidinamide derivative since the suitable pH range is wide and thus the convenience is greater when cobalt is industrially extracted. Regarding pH, it is preferred that, with the pH of an acid aqueous solution comprising cobalt and manganese adjusted to 3.5 or more and 5.5 or less, an organic solution of an extraction agent be added thereto, and it is more preferred that, with the above pH adjusted to 4.0 or more and 5.0 or less, an organic solution of an extraction agent be added thereto. When the pH is less than 3.5, there is a possibility that cobalt cannot be sufficiently extracted depending on the types of extraction agent. When the pH is above 5.5, there is a possibility that not only cobalt but also manganese is extracted depending on the types of extraction agent.

The mechanism in which the extraction agent of the present invention has an extraction behavior different from conventional extraction agents is not accurately grasped, and it is thought that the effects which conventional extraction agents do not have are obtained by the structural characteristics of the extraction agent of the present invention.

EXAMPLES

The present invention will now be described in more detail by way of examples. It should be noted, however, that the present invention is not restricted to these descriptions.

Example 1

Synthesis of Glycinamide Derivatives

As an example of amide derivatives forming an extraction agent, a glycinamide derivative represented by the following general formula (I) was synthesized, that is, N—[N,N-bis(2-ethylhexyl)aminocarbonylmethyl]glycine (or also referred to as N,N-di(2-ethylhexyl)acetamide-2-glycine), hereinafter referred to as "D2EHAG"), into which two 2-ethylhexyl groups are introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were collected. These were dissolved by adding chloroform, and 13.5 g (0.12 mol) of 2-chloroacetyl chloride was then added by drops thereto, followed by washing with 1 mol/l hydrochloric acid once. After this, washing was carried out with ion exchanged water and the chloroform phase was collected.

Next, anhydrous sodium sulphate was added in a suitable amount (approximately 10 to 20 g) for dehydration, followed by filtration to obtain 29.1 g of yellow liquid. When the structure of this yellow liquid (reaction product) was identified using a nuclear magnetic resonance spectrometer (NMR), the above yellow liquid was confirmed to have the structure of 2-chloro-N,N-di(2-ethylhexyl)acetamide (hereinafter referred to as "CDEHAA"). The percent yield of CDEHAA was 90% relative to di(2-ethylhexyl)amine, a raw material.

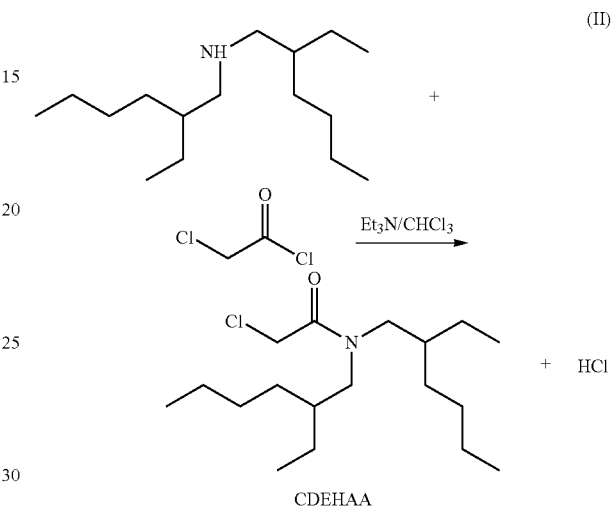

Next, as shown in the following reaction formula (III), 8.0 g (0.2 mol) of sodium hydroxide was dissolved by adding methanol, and 15.01 g (0.2 mol) of glycine was further added thereto. While stirring the obtained solution, 12.72 g (0.04 mol) of the above CDEHAA was slowly added by drops thereto and stirred. After completion of stirring, the solvent in the reaction liquid was distilled off, and the residue was dissolved by adding chloroform. To this solution, 1 mol/l sulphuric acid was added for acidification, followed by washing with ion exchanged water, and the chloroform phase was collected.

Figure 2:
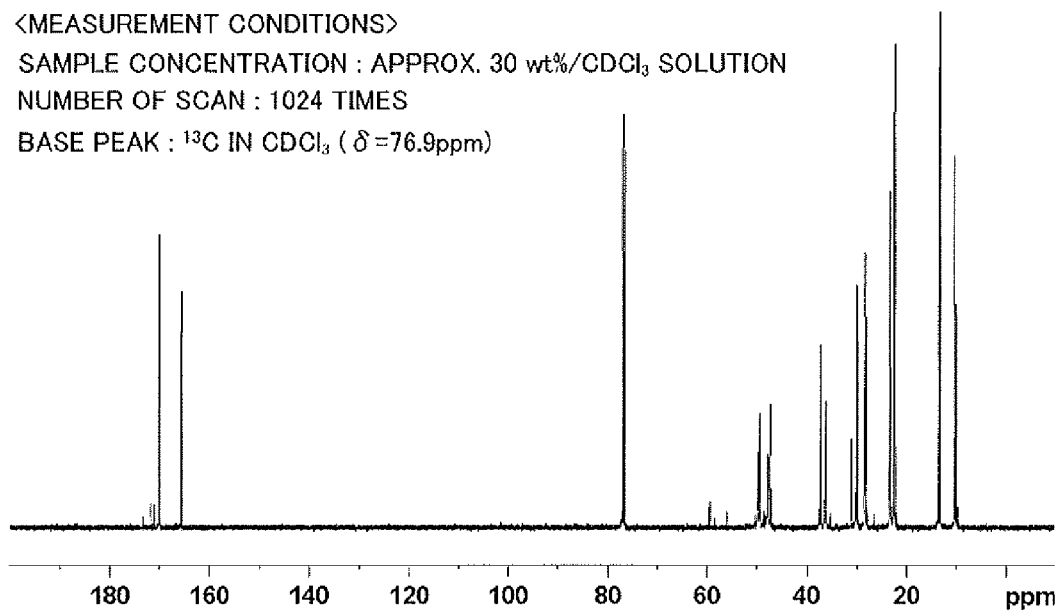
FIG. 2 is a figure showing a $^{13}$C-NMR spectrum of a glycinamide derivative synthesized in Example 1.

To this chloroform phase, anhydrous magnesium sulphate was added in a suitable amount for dehydration, followed by filtration. The solvent was removed under reduced pressure again to obtain 12.5 g of yellow paste. The percent yield based on the amount of the above CDEHAA was 87%. When the structure of the yellow paste was identified by NMR and elemental analysis, the paste was confirmed to have the structure of D2EHAG as shown in FIG. 1 and FIG. 2. The above steps were carried out to obtain a valuable metal extraction agent of Example 1.

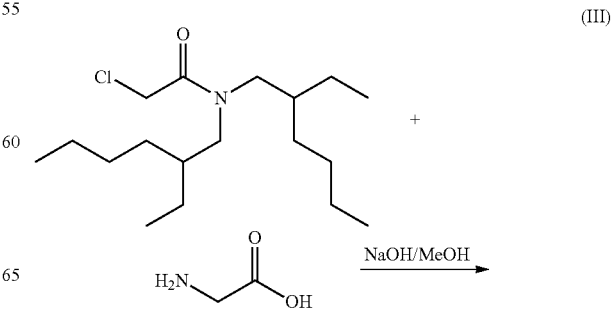

-continued

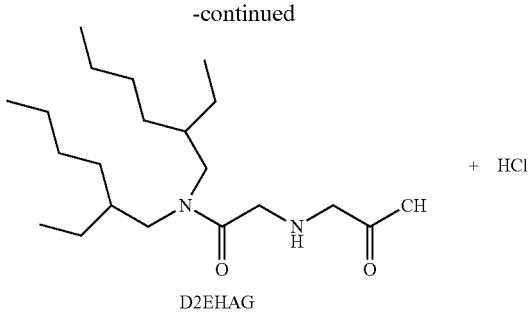

D2EHAG

Example 2

Synthesis of N-methylglycine Derivatives

As another example of amide derivatives forming an extraction agent, an N-methylglycine derivative represented by the following general formula (I) was synthesized, that is, N-[N,N-bis(2-ethylhexyl)aminocarbonylmethyl]sarcosine (or also referred to as N,N-di(2-ethylhexyl)acetamide-2-sarcosine), hereinafter referred to as "D2EHAS"), into which two 2-ethylhexyl groups are introduced.

D2EHAS was synthesized as follows. As shown in the following reaction formula (IV), 5.3 g (0.132 mol) of sodium hydroxide was dissolved by adding methanol, and 11.8 g (0.132 mol) of sarcosine (N-methylglycine) was also added thereto. While stirring the obtained solution, 36.3 g (0.12 mol) of the above CDEHAA was slowly added by drops thereto and stirred. After completion of stirring, the solvent in the reaction liquid was distilled off, and the residue was dissolved by adding chloroform. To this solution, 1 mol/l sulphuric acid was added for acidification, followed by washing with ion exchanged water, and the chloroform phase was collected.

To this chloroform phase, anhydrous magnesium sulphate was added in a suitable amount for dehydration, followed by filtration. The solvent was removed under reduced pressure again to obtain 26.8 g of yellowish brown paste. The percent yield based on the amount of the above CDEHAA was 60%. When the structure of the yellow paste was identified by NMR and elemental analysis, the paste was confirmed to have the structure of D2EHAS. The above steps were carried out to obtain a valuable metal extraction agent of Example 2.

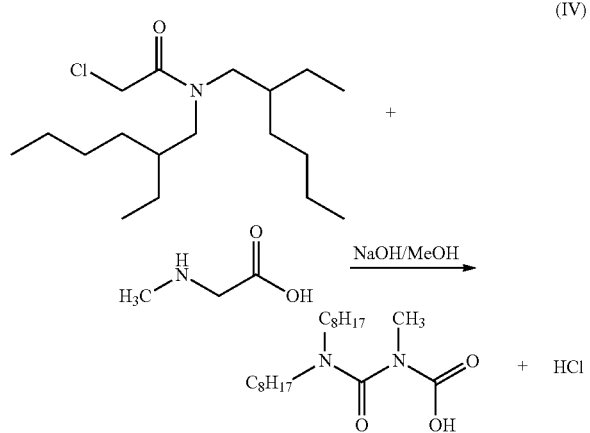

(IV)

Example 3

Synthesis of Histidinamide Derivatives

As another example of amide derivatives forming an extraction agent, a histidinamide derivative represented by the following general formula (I) was synthesized, that is, N-[N,N-bis(2-ethylhexyl)aminocarbonylmethyl]histidine (or also referred to as N,N-di(2-ethylhexyl)acetamide-2-histidine), hereinafter referred to as "D2EHAH"), into which two 2-ethylhexyl groups are introduced.

D2EHAH was synthesized as follows. As shown in the following reaction formula (V), 16 g (0.4 mol) of sodium hydroxide was dissolved by adding methanol, and 31.0 g (0.2 mol) of histidine was also added thereto. While stirring the obtained solution, 13.2 g (0.04 mol) of the above CDEHAA was slowly added by drops thereto. After completion of the drop-by-drop addition, stirring was carried out with alkaline conditions maintained. After completion of stirring, the solvent in the reaction liquid was distilled off, and the residue was dissolved by adding ethyl acetate. This solution was washed, and the ethyl acetate phase was collected.

To this ethyl acetate phase, anhydrous magnesium sulphate was added in a suitable amount for dehydration, followed by filtration. The solvent was removed under reduced pressure again to obtain 9.9 g of yellowish brown paste. The percent yield based on the amount of the above CDEHAA was 57%. When the structure of the yellowish brown paste was identified by NMR and elemental analysis, the paste was confirmed to have the structure of D2EHAH. The above steps were carried out to obtain a valuable metal extraction agent of Example 3.

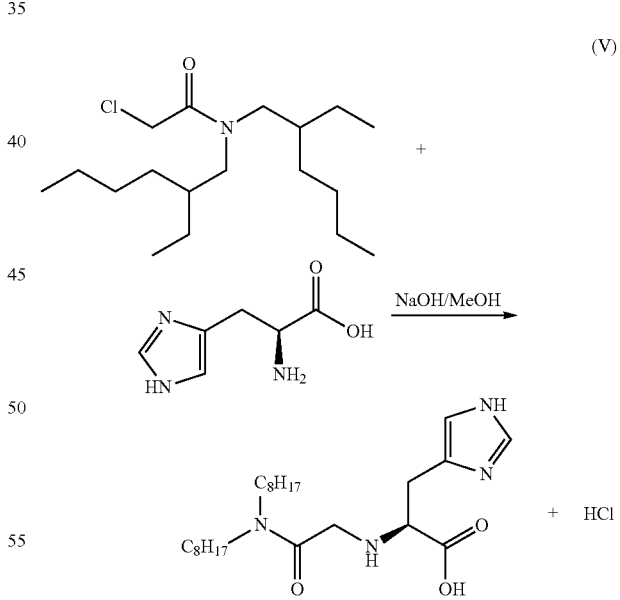

(V)

Comparative Example 1

As a valuable metal extraction agent of Comparative Example 1, a commercially available carboxylic acid-based cobalt extraction agent (Product name: VA-10, neodecanoic acid, manufactured by Hexion Specialty Chemicals Japan) was used.

Comparative Example 2

As a valuable metal extraction agent of Comparative Example 2, N,N-dioctyl-3-oxapentan-1,5-amic acid (hereinafter referred to as "DODGAA"), a conventionally known europium extraction agent was used.

DODGAA was synthesized as follows. First, as shown in the following reaction formula (VI), 4.2 g of anhydrous diglycolic acid was put into a round bottom flask, and 40 ml of dichloromethane was put therein and suspended. After that, 7 g of dioctylamine (purity 98%) was dissolved in 10 ml of dichloromethane, and the obtained solution was slowly added thereto using a dropping funnel. While stirring the solution at room temperature, the solution was confirmed to become clear by the reaction of anhydrous diglycolic acid, and the reaction was completed.

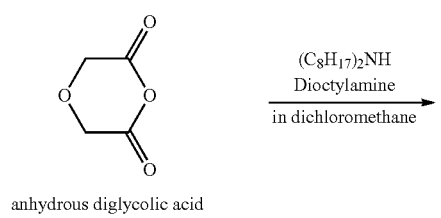

anhydrous diglycolic acid (VI)

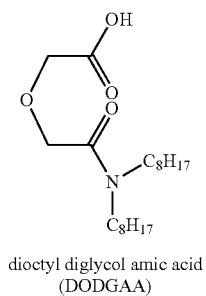

dioctyl diglycol amic acid
(DODGAA)

Subsequently, the above solution was washed with water to remove water-soluble impurities. After washing with water, sodium sulphate was added to the solution as a dehydrating agent. The solution was subjected to suction filtration, and the solvent was then vaporized. Recrystallization was carried out with hexane (three times), followed by vacuum drying. The yield of the obtained substance was 9.57 g, and the percent yield based on the above anhydrous diglycolic acid was 94.3%. When the structure of the obtained substance was identified by NMR and elemental analysis, the substance was confirmed to be DODGAA with a purity of 99% or more.

Extraction of Cobalt

Cobalt was extracted and separated using the valuable metal extraction agents of Examples 1 to 3 and Comparative Example 1.

Examples 1 to 3

Several types of acid solution of sulphuric acid comprising cobalt and manganese each in an amount of $1 \times 10^{-4}$ mol/l and being adjusted to pH 2.5 to 7.5, and an equal volume of an n-dodecane solution comprising 0.01 mol/l of a valuable metal extraction agent were added together in test tubes, and the test tubes were put into a constant temperature oven at 25° C. and shaken for 24 hours. At this time, the pH of the sulphuric acid solution was adjusted using 0.1 mol/l sulphuric acid, ammonium sulphate and ammonia.

Figure 3:
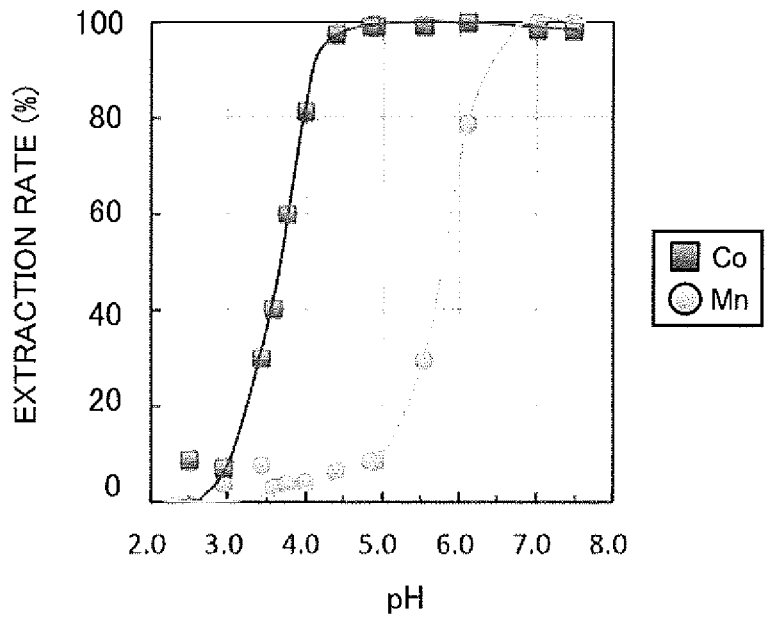
FIG. 3 shows the results of the extraction of cobalt from an acid solution comprising cobalt and manganese using the valuable metal extraction agent of Example 1.
Figure 4:
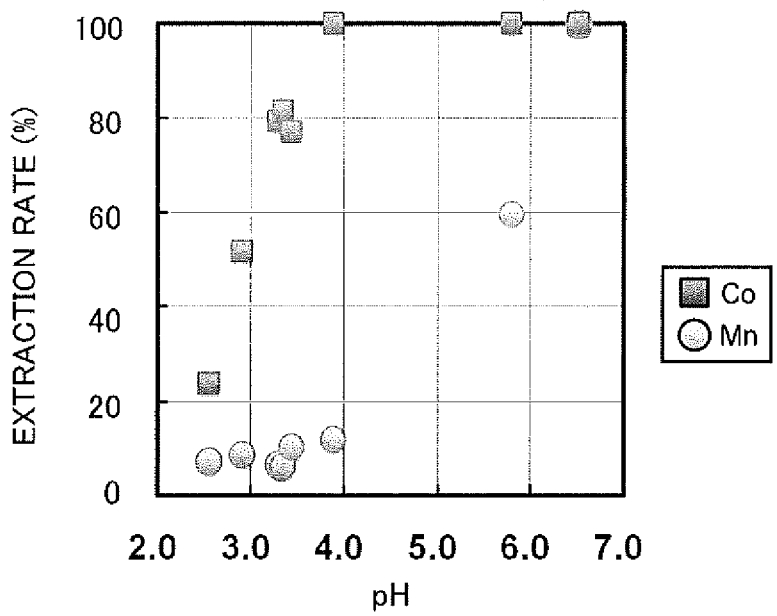
FIG. 4 shows the results of the extraction of cobalt from an acid solution comprising cobalt and manganese using the valuable metal extraction agent of Example 2.
Figure 5:
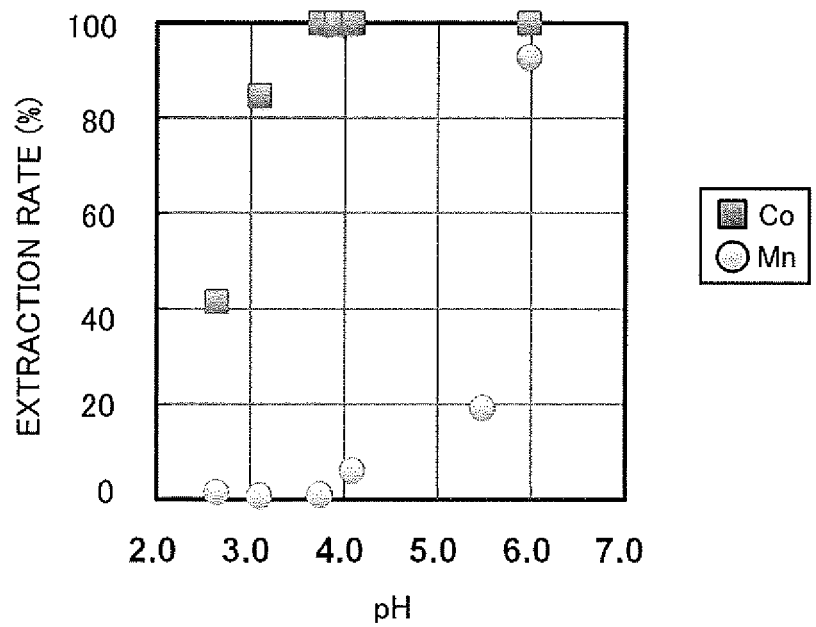
FIG. 5 shows the results of the extraction of cobalt from an acid solution comprising cobalt and manganese using the valuable metal extraction agent of Example 3.

After shaking, the aqueous phase was collected, and the cobalt concentration and the manganese concentration were measured using inductively coupled plasma-atomic emission spectroscopy (ICP-AES). The organic phase was subjected to back extraction using 1 mol/l sulphuric acid. The cobalt concentration and the manganese concentration in the back extraction phase were measured using ICP-AES. From these measurement results, the extraction rates of cobalt and manganese were defined as the amount of material in the organic phase/(the amount of material in the organic phase+the amount of material in the aqueous phase) and measured. The results of the use of the valuable metal extraction agent of Example 1 are shown in FIG. 3, the results of the use of the valuable metal extraction agent of Example 2 are shown in FIG. 4, and the results of the use of the valuable metal extraction agent of Example 3 are shown in FIG. 5. In FIGS. 3 to 5, the abscissa is the pH of an acid solution of sulphuric acid, and the ordinate is the extraction rate (unit: %) of cobalt or manganese. In the graphs, the square indicates the extraction rate of cobalt and the circle indicates the extraction rate of manganese.

Comparative Example 1

Figure 6:
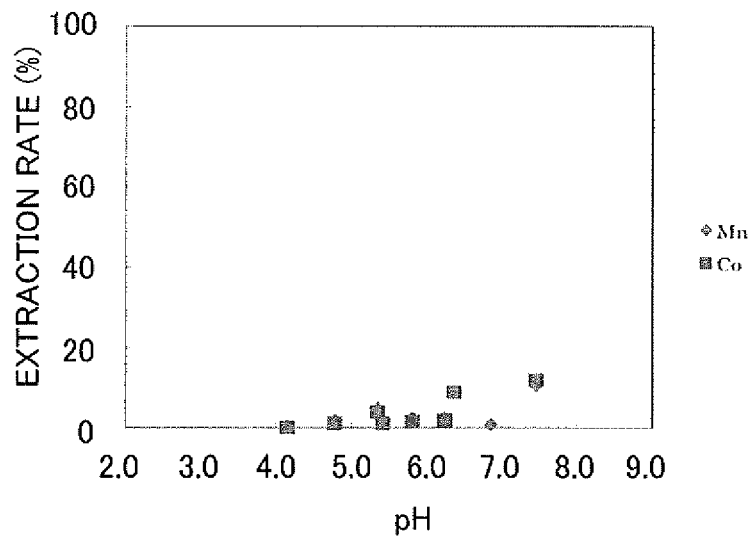
FIG. 6 shows the results of the extraction of cobalt from an acid solution comprising cobalt and manganese using the valuable metal extraction agent of Comparative Example 1.

Cobalt was extracted by the same method as in the Examples except that the pH of an acid solution of sulphuric acid was adjusted to 4.0 to 7.5 and the concentration of the n-dodecane solution comprising the valuable metal extraction agent was changed to 0.1 mol/l, which is ten times the concentration in the Examples. The results are shown in FIG. 6. In FIG. 6, the abscissa is the pH of an acid solution of sulphuric acid, and the ordinate is the extraction rate (unit: %) of cobalt or manganese. In the graph, the square indicates the extraction rate of cobalt and the diamond indicates the extraction rate of manganese.

It was recognized that by using the valuable metal extraction agents of the Examples, cobalt could be extracted at an extraction rate of at least above 20% in a pH range of 3.0 or more to 5.5 or less (FIG. 3 to FIG. 5). In particular, it was recognized that by using an N-methylglycine derivative or a histidinamide derivative, the suitable pH range was wide, and convenience was greater when industrially carrying out the cobalt extraction of the present invention (FIG. 4, FIG. 5). It was also recognized that cobalt could be extracted at an extraction rate of above 80% and manganese was hardly extracted in a pH range of 4.0 or more to 5.0 or less regardless of the types of derivative (FIG. 3 to FIG. 5). Meanwhile, it was recognized that by using the valuable metal extraction agent of Comparative Example 1, cobalt could be extracted only at an extraction rate of less than 20% even when the concentration of the extraction agent was ten times that in the Examples (FIG. 6).

The invention claimed is:
1. A cobalt extraction method, wherein an acid solution containing manganese and cobalt is subjected to solvent extraction by a valuable metal extraction agent comprising an amide derivative represented by general formula (I) to extract the cobalt from the acid solution:

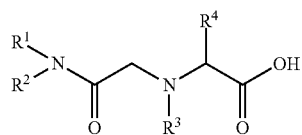

(I)

wherein, $R^1$ and $R^2$ each represent the same or different alkyl groups; the alkyl group is optionally a straight chain or a branched chain; $R^3$ represents a hydrogen atom or an alkyl group; and $R^4$ represents a hydrogen atom or any group other than an amino group, which is bound to the α carbon as an amino acid.

2. The cobalt extraction method according to claim 1, wherein the amide derivative is any one or more of glycinamide derivatives, histidinamide derivatives, lysinamide derivatives, aspartic acid amide derivatives and N-methylglycine derivatives.

3. The cobalt extraction method according to claim 1 or 2, wherein the acid solution is subjected to the solvent extraction with the pH of the acid solution adjusted to a range of 3.5 to 5.5.

4. A cobalt extraction agent comprising an amide derivative represented by general formula (I):

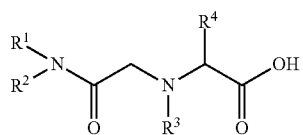

(I)

wherein, $R^1$ and $R^2$ each represent the same or different alkyl groups;

the alkyl group is optionally a straight chain or a branched chain;

$R^3$ represents a hydrogen atom or an alkyl group; and $R^4$ represents a hydrogen atom or any group other than an amino group, which is bound to the α carbon as an amino acid.

* * * * *